United States Patent [19]
Schneider et al.

[11] Patent Number: 5,091,343
[45] Date of Patent: Feb. 25, 1992

[54] CONTAINER FOR HOLDING EQUIPMENT DURING STERILIZATION

[75] Inventors: Edward T. Schneider; Norman L. Siegel, both of Mentor; Raymond C. Kralovic, Austinburg, all of Ohio

[73] Assignee: Steris Corporation, Mentor, Ohio

[21] Appl. No.: 349,304

[22] Filed: May 9, 1989

Related U.S. Application Data

[63] Continuation-in-part of Ser. No. 140,388, Jan. 4, 1988, Pat. No. 4,892,706, which is a continuation-in-part of Ser. No. 826,730, Feb. 6, 1986, Pat. No. 4,731,222.

[51] Int. Cl.$^5$ .......................... A61L 2/18; B08B 13/00
[52] U.S. Cl. ...................... 422/297; 134/95; 134/99; 134/102; 422/292; 422/300
[58] Field of Search ................ 422/292, 297, 300; 134/95, 99, 102

[56] References Cited

U.S. PATENT DOCUMENTS

| | | | |
|---|---|---|---|
| 1,861,768 | 6/1932 | Wappler. | |
| 1,939,715 | 12/1933 | Meitzler. | |
| 2,715,251 | 8/1955 | Vischer, Jr. | |
| 3,429,653 | 2/1969 | Brett. | |
| 3,893,832 | 8/1975 | Perry et al. | 55/268 |
| 4,247,517 | 1/1981 | Sanderson et al. | 422/26 |
| 4,296,862 | 10/1981 | Armentrout et al. | 206/439 |
| 4,512,498 | 4/1985 | Leibinger | 220/371 |
| 4,551,311 | 11/1985 | Lorenz | 422/300 |
| 4,552,728 | 11/1985 | Taylor | 422/300 |
| 4,617,065 | 10/1986 | Sundheimer | 134/25.4 |
| 4,617,178 | 10/1986 | Nichols | 422/310 |
| 4,661,326 | 4/1987 | Schainholz | 422/310 |
| 4,671,943 | 6/1987 | Wahlquist | 422/300 |
| 4,704,254 | 11/1987 | Nichols | 422/28 |
| 4,731,222 | 3/1988 | Kralovic et al. | 422/28 X |

FOREIGN PATENT DOCUMENTS

| | | |
|---|---|---|
| 3128029 | 2/1983 | Fed. Rep. of Germany. |
| 3405268 | 9/1985 | Fed. Rep. of Germany. |
| 2165754 | 4/1986 | United Kingdom. |

Primary Examiner—Jill Johnston
Attorney, Agent, or Firm—Fay, Sharpe, Beall, Fagan, Minnich & McKee

[57] ABSTRACT

A liquid sterilizing system (A) defines a basin (10) in which a container (B) is removably disposed. The liquid sterilizing system selectively pumps sterile rinse liquids from a supply (24) and liquid sterilant solutions from a supply (70) into the basin filling the basin and the container. The container includes a lower shell having a bottom wall (34) that defines an aperture (32) for receiving sterilant and sterile rinse liquids. A nozzle plate (44) is mounted close to but spaced from the shell bottom wall to define a tortuous liquid distribution path (40) between the inlet aperture and nozzle plate apertures (90). A barrier (96) divides the liquid receiving portion and a drain portion of the liquid distribution path between the shell bottom surface and the nozzle plate. A cover (80) has a downward depending peripheral wall (82) which is offset from the shell peripheral wall (86) by the spacers (88) to define a tortuous vent path (48) therethrough. The container is lifted out by handles (100) which enable the container to be removed without disturbing the transparent cover, hence, without disturbing the sterile condition of the items within the container. In this manner, the sterilized items can be inventoried and maintained sterilized in the container for an extended duration.

23 Claims, 4 Drawing Sheets

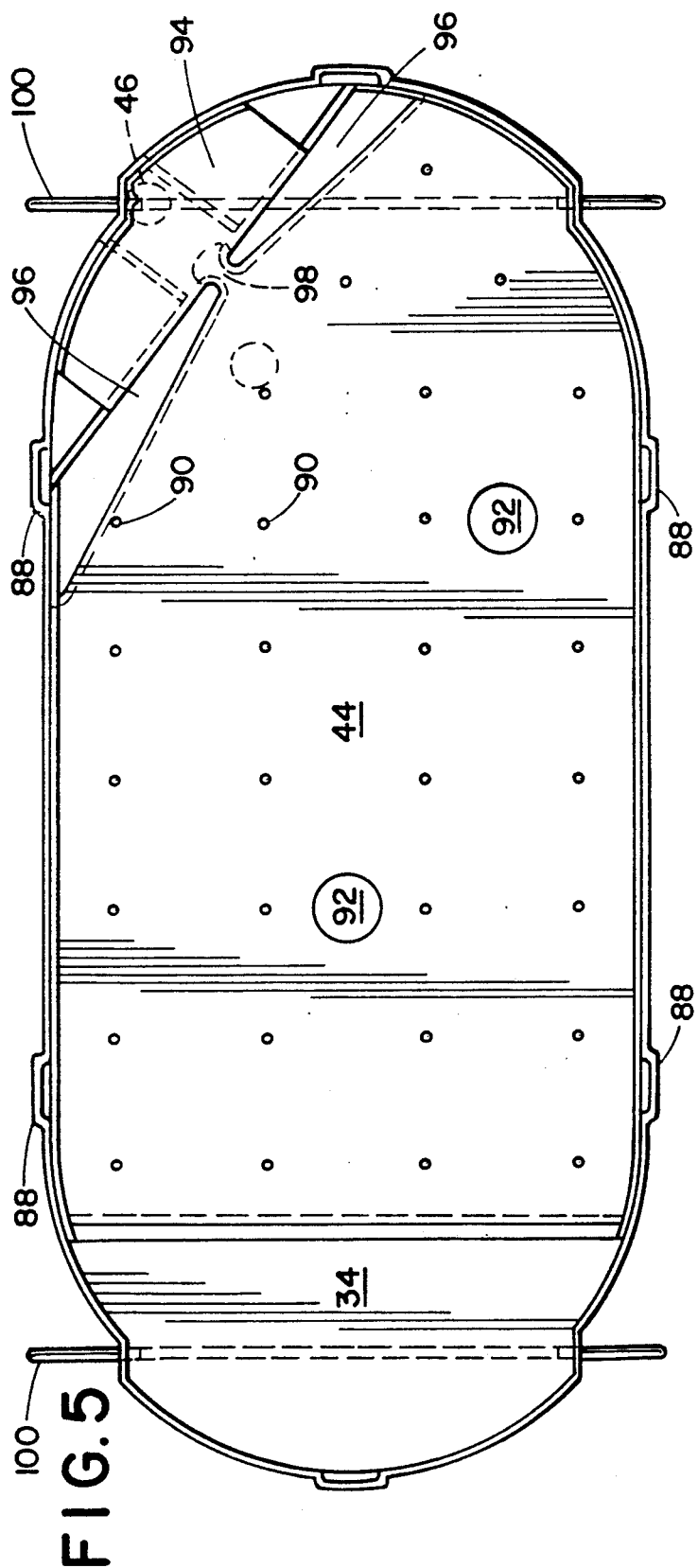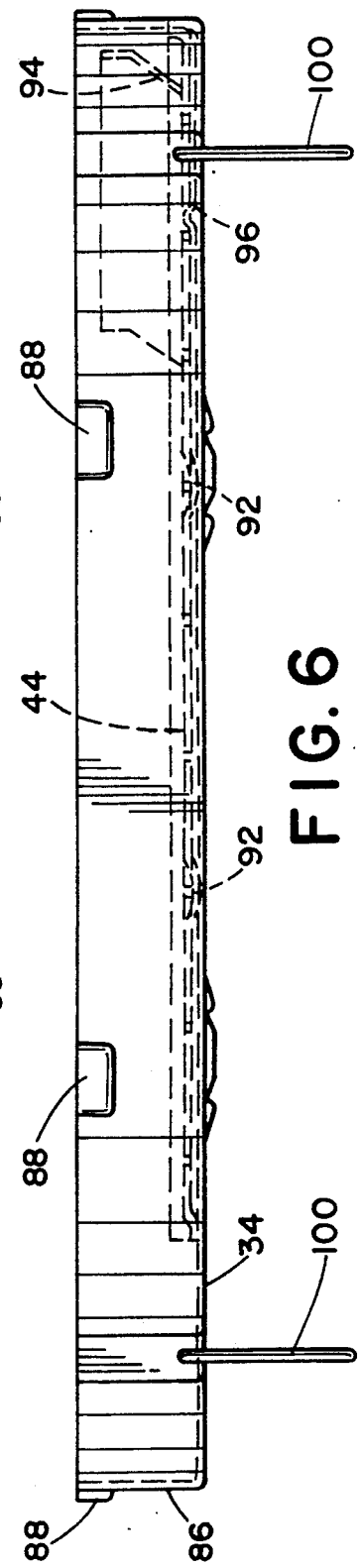

CONTAINER FOR HOLDING EQUIPMENT DURING STERILIZATION

The present invention is a continuation-in-part of U.S. patent application Ser. No. 140,388, filed Jan. 4, 1988, now U.S. Pat. No. 4,892,706, which, in turn, is a continuation-in-part of patent application Ser. No. 826,730, filed Feb. 6, 1986, now U.S. Pat. No. 4,731,222.

BACKGROUND OF THE INVENTION

The present invention pertains to the art of microbial decontamination. It finds particular application in conjunction with sterilizing medical equipment and will be described with particular reference thereto. It will be appreciated, however, that the invention is also applicable to disinfecting systems as well as to microbially decontaminating a wide range of items, including dental instruments, endoscopes, laboratory equipment, manufacturing equipment, and other equipment and items on which it is desirable to eliminate microbial life forms.

Sterilization connotes the absence of all life forms, including bacterial endospores which are the living organisms most resistant to conventional sterilants. Disinfection, by distinction, only connotes the absence of pathogenic life forms. Microbial decontamination is generic to both sterilization and disinfection.

Most medical equipment is sterilized at high temperatures. Commonly, the equipment is sterilized in a steam autoclave under a combination of high temperature and pressure. Endoscopes, rubber and plastic devices or portions of devices, such as lenses, and the like may be destroyed or have their useful lives severely curtailed by this heat and pressure.

The more sensitive medical equipment is often sterilized with ethylene oxide, which is thermally less severe than steam. The items must be exposed to the ethylene oxide for a relatively long time, on the order of three and a half hours. Thereafter, eight to twelve hours are normally required for de-gassing or desorbing the ethylene oxide from plastic and other materials which are capable of absorbing the ethylene oxide. The pressurization and depressurization cycles of ethylene oxide sterilization may damage lens systems and other delicate instruments. Moreover, the ethylene oxide is relatively expensive. It is sufficiently toxic and volatile that extensive precautions are commonly taken to assure operator safety.

Liquid systems are commonly used for disinfection of heat sensitive or other delicate instruments. Using liquid sterilants to achieve disinfection is normally rapid, cost effective, and does minimal damage to medical devices. Commonly, a technician mixes a sterilant composition and manually immerses the item to be sterilized. The immersion is timed manually by the technician. Technician variation, liquid sterilant shelf life, and the like raise problems with assurance and reproducibility of the disinfection. Rinsing of the items to remove chemical residues also adds a variable that reduces the assurance of disinfection or sterility. Once the sterilant solution is rinsed, the item is susceptible to reinfection by air borne microbes.

In accordance with the present invention, a new and improved sterilization apparatus, system, and method are provided which overcomes the above referenced problems and others.

SUMMARY OF THE INVENTION

In accordance with one aspect of the present invention, a liquid sterilizing or disinfecting system is provided. A sloping container-receiving basin contains a vent aperture adjacent an upper most end, a drain aperture adjacent a lower most end, and a liquid inlet. A lid selectively seals the basin when in a closed position and opens to provide ready access to the basin. A container for receiving articles to be microbially decontaminated is removably disposed in the basin. A liquid sterilant supply means supplies a liquid antimicrobial solution and a sterile rinse supply means supplies a sterile rinse liquid. A drain is connected with the basin drain aperture for draining antimicrobial and rinse liquids from the basin. A means is provided for selectively opening and closing the drain to drain liquids from the basin and retain liquids in the basin. A pump selectively pumps volumes of liquid antimicrobial solution from the liquid antimicrobial solution supply means and volumes of sterile rinse liquid from the rinse supply means to the liquid inlet for filling the container and displacing the air therefrom.

In accordance with another aspect of the invention, the container includes an outer lower shell having a bottom surface and a peripheral wall. The shell defines a drain aperture adjacent to the basin lower most portion and defines a liquid receiving aperture in fluid communication with the basin liquid inlet. A nozzle plate defines a tortuous inlet path from the liquid receiving aperture to a plurality of nozzles distributed around the lower shell. The inlet path is sufficiently tortuous that migration of contaminating microbes in ambient air after removal from the basin is inhibited. A container cover has a top surface and downward depending flanges which engage the shell to close the container. At least one of the shell and cover is configured to define a tortuous vent path from at least an upper most portion of the container when disposed in the basin such that received liquids displace substantially all air from the container through the vent path.

One advantage of the present invention is that it facilitates effective sterilization of medical and other items with liquid sterilants.

Another advantage of the present invention is that it maintains the sterile condition of the items during temporary or longer term storage.

Yet another advantage of the present invention is that it facilitates maintaining an organized inventory of sterilized items.

Still further advantages of the present invention will become apparent to those of ordinary skill in the art upon reading and understanding the following detailed description.

BRIEF DESCRIPTION OF THE DRAWINGS

The invention may take form in various parts and arrangements of parts. The drawings are only for purposes of illustrating a preferred embodiment and are not to be construed as limiting the invention.

FIG. 5 is a top view of the container lower shell with the cover removed; and,

FIG. 6 is a side view of the shell of FIG. 5.

DETAILED DESCRIPTION OF THE PREFERRED EMBODIMENT

Figure 1:
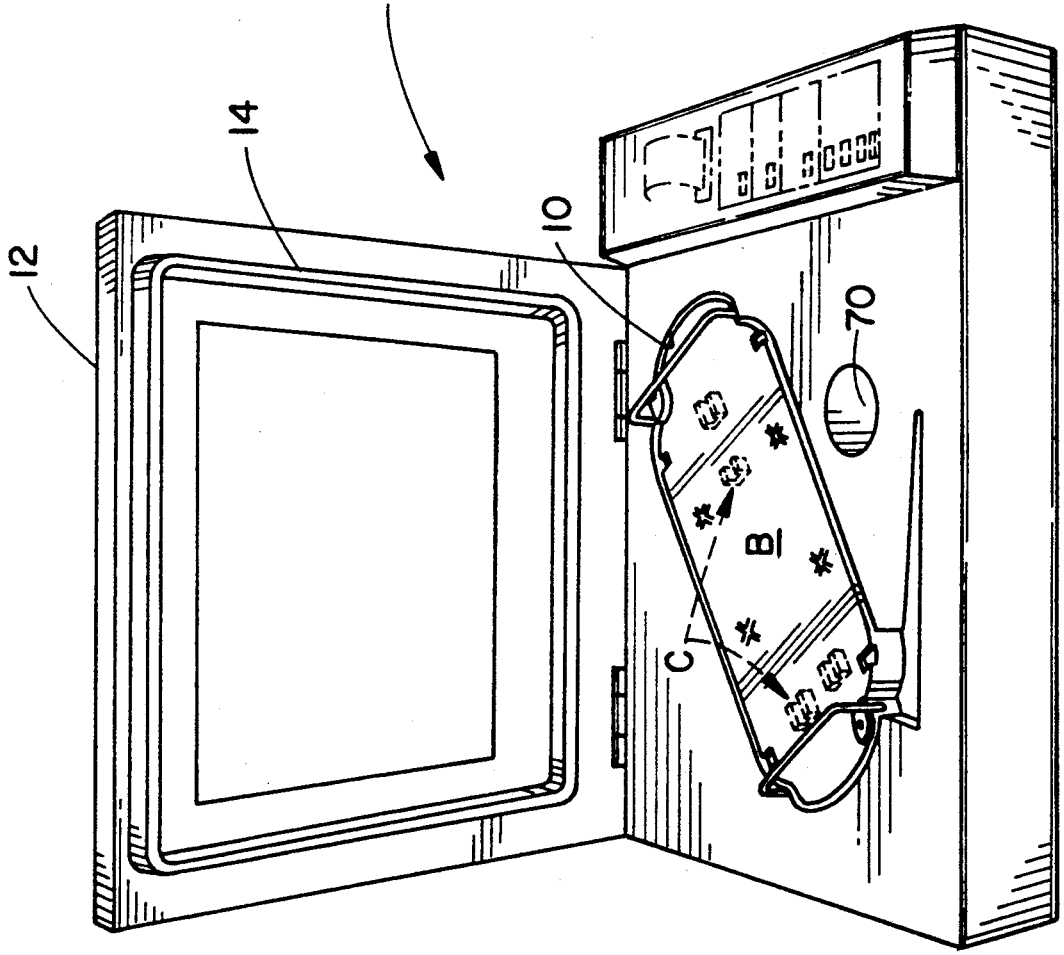
FIG. 1 is a perspective view of a microbial decontamination system in accordance with the present invention.

With reference to FIG. 1, a sterilizing apparatus A defines a basin for removably receiving one of a plurality of containers B. Each container may be configured or fitted with appropriate mounting structures C for holding or arranging medical instruments or other items. After the container is placed in the basin, a lid 12 is closed causing a gasket 14 to seal the basin and container from the ambient atmosphere. The sterilizing apparatus in a carefully controlled cycle floods the basin filling the container and surrounding the medical instruments, container, or other items to be sterilized with a liquid sterilant or other antimicrobial solution. The sterilant solution is drained and a sterile rinse fills the basin and container to remove chemical residue. After the rinse has been drained, the lid is opened and the container is removed as a unit containing sterilized items. The container is configured such that it permits the ingress and egress of liquid sterilant and rinse solutions but prevents microbial contamination in the ambient air from reaching the enclosed medical instruments or other items. The container with the contained sterilized items may be inventoried and stored until the sterile items are needed.

Figure 2:
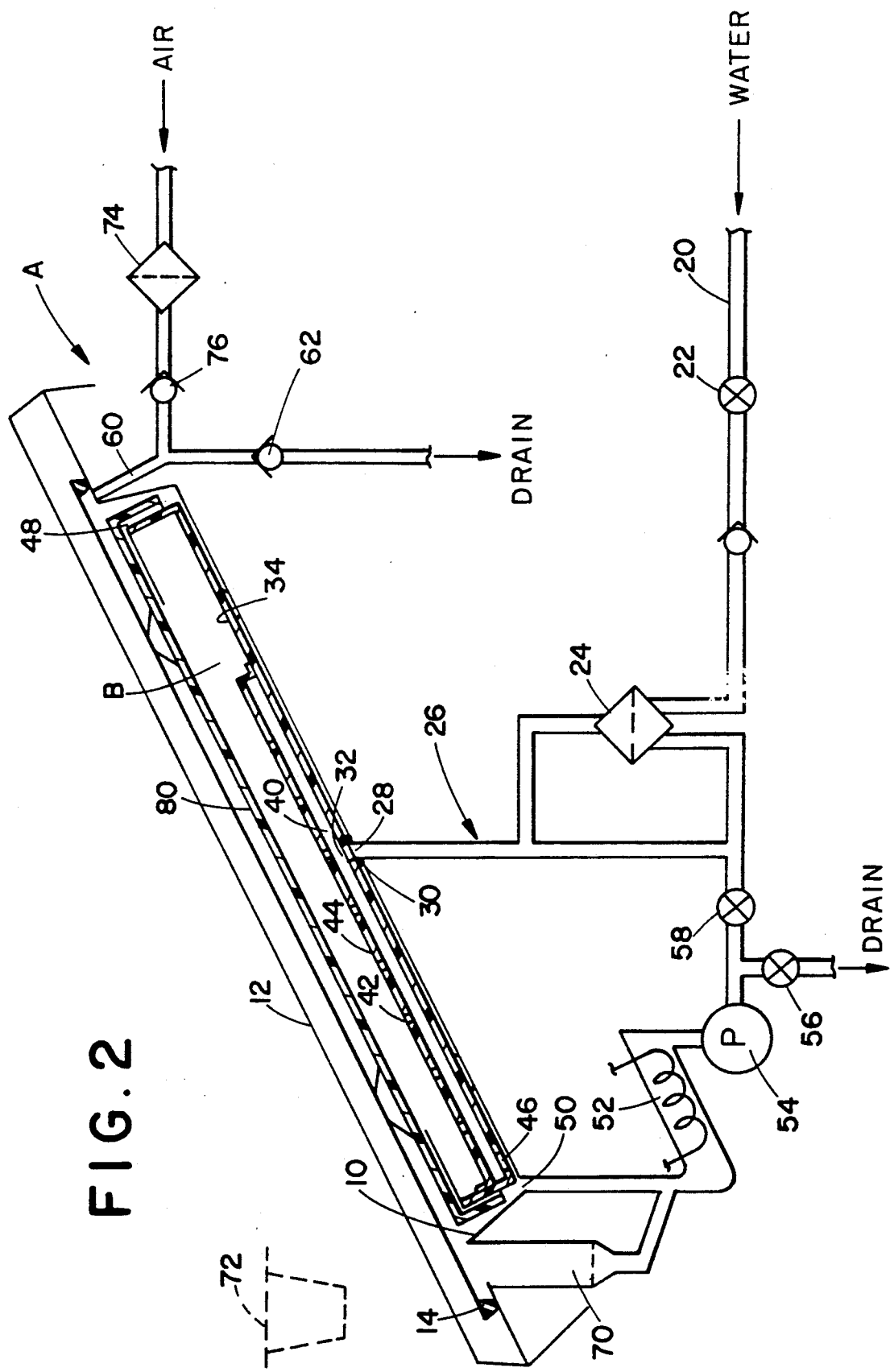
FIG. 2 is a diagrammatic illustration of the fluid flow paths for the system of FIG. 1.

With reference to FIG. 2, water, such as tap water, is received at an inlet 20. A valve 22 selectively enables the water to flow to a sterilizing means 24 for sterilizing the received water. In the preferred embodiment, the sterilizing means is a filter which mechanically separates microbes and other contaminants from the received water. When the valve 22 is opened, incoming water flows through the filter 24 becoming sterilized and flows through a tubing system 26 to a basin inlet 28. A seal 30 directs water into a liquid receiving inlet 32 in a lower wall 34 of the container B.

The liquid flows through a tortuous path 40 defined between the bottom wall 34 and apertures 42 in a baffle plate 44 of the container. The liquid flows into the interior of the container immersing the items to be sterilized. Liquid flows out of the container through a container drain outlet 46 and vent passage 48 and the tubing system 26 conveys the fluid from a basin drain outlet 50 to a heater 52 and a pump 54. A drain valve 56 selectively enables the fluid to be drained from the system. A recirculating valve 58 allows the pump to pump the fluid through the tubing system back to the fluid inlet 28. As additional sterile water flows into the system, air is displaced through a vent passage or vent outlet 50 which is connected by a check valve 62 with the drain.

The received liquid also fills a well 70 which defines a reagent receiving chamber for receiving antimicrobial agents, wetting agents, detergents, and other treatment chemicals for improving the cleaning and sterilizing effect. An ampule 72 contains peracetic acid or other strong oxidant compositions or reagents which react to form strong oxidants, as well as buffers and corrosion inhibitors to be introduced into the well. After the system is filled with water, inlet valve 22 is closed. The recirculating valve 58 is opened and the pump 54 is actuated. As fluid is drawn through the well by the pump, the reagents mix with the water forming a sterilizing or other antimicrobial solution. The sterilizing solution is circulated through the tubing system 26 back to the inlet 28 through the tortuous path 40 and distributed among the many inlets of the baffle plate 44. As the pump 54 circulates the sterilant solution, some of the sterilant flows through the sterilizing filter 24 sterilizing it. Other solution flows through the vent 60 and other tubing and fluid contacting surfaces.

After the sterilant solution has been maintained in contact with the items in the container and all tubing valve and other surfaces between the sterilizing means 24 for a selected duration, the recirculation valve 58 is closed and the drain valve 56 is opened. The antimicrobial solution is pumped or drained from the system. In this manner, all the tubing and valve surfaces with which the sterile rinse fluid comes in contact are sterilized by the sterilant solution. More specifically, the fill valve 20 is again opened so that tap water flows through filter 24 through the sterilized tubing system 26 to the fluid inlet 28. The sterile rinse solution continues to flow into the basin 10 until all the air is displaced. Pump 54 may be actuated again to recirculate the rinse solution for a preselected duration. Thereafter, the drain valve 56 is opened and the rinse solution is drained. Air flows through a check valve 76 and the sterilizing filter 74 such that sterile air fills the basin and container as the rinse and sterilant solutions are drained.

Figure 3:
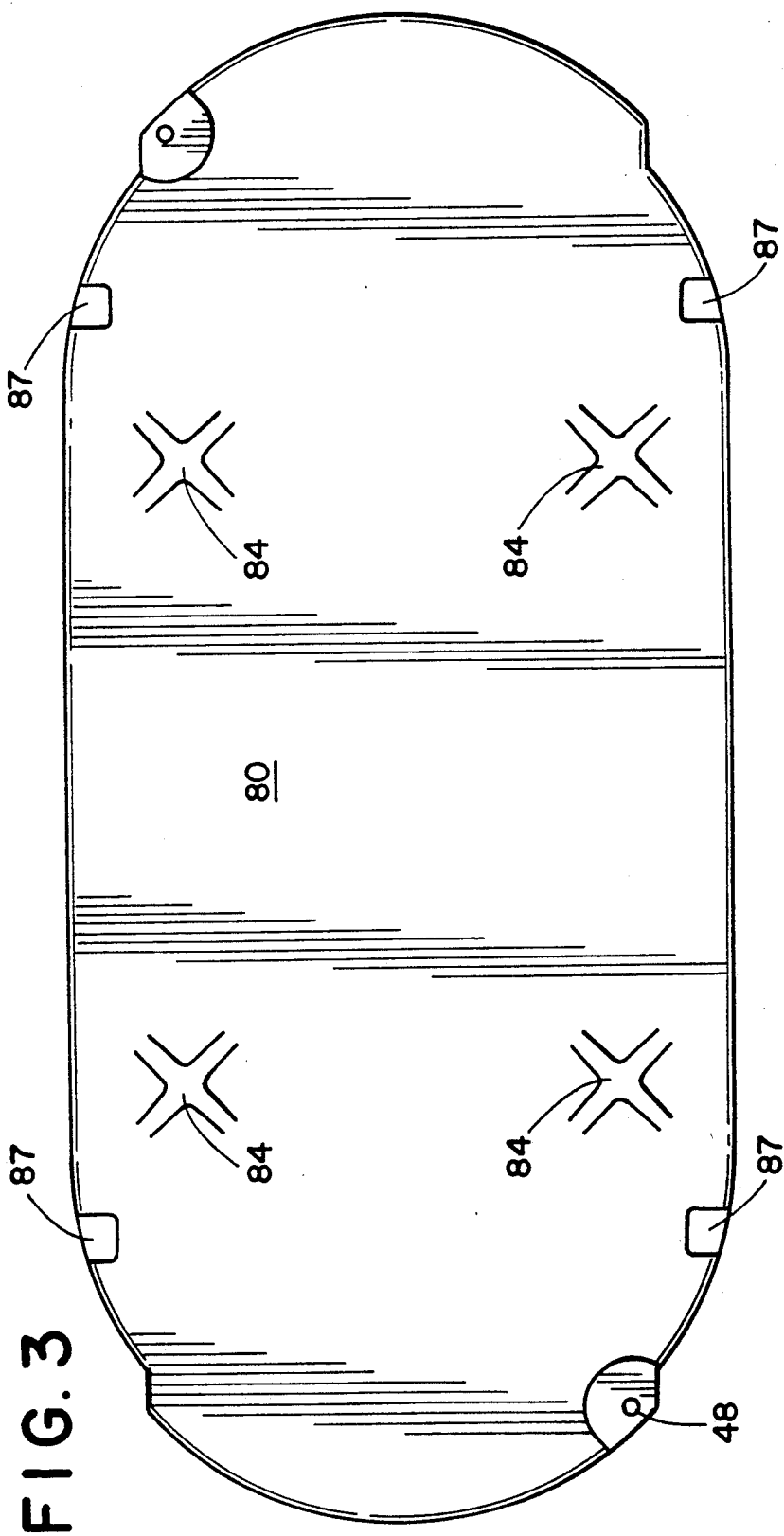
FIG. 3 is a top view of the container, particularly the container cover.
Figure 4:
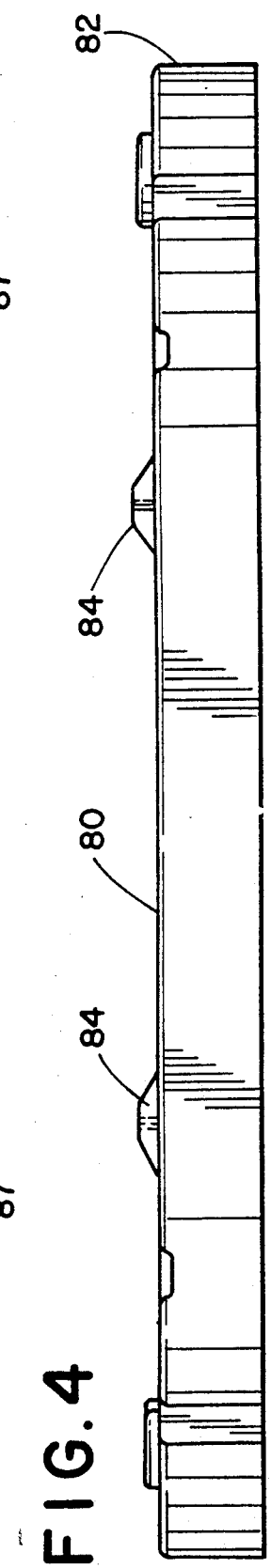
FIG. 4 is a side view of the cover.

With reference to FIGS. 3 and 4, the container B has a generally flat cover 80 with a downward depending peripheral wall 82 extending peripherally therearound. Spacers 84 extend upward from the container cover to engage the sterilizer lid such that lid urges the container into firm engagement with the sealing means 28. The spacers are configured such that no air is trapped by the spacers or the interaction between the spacers and the sterilizer lid. Rather, all surfaces around the spacers become immersed in the sterilant solution and are sterilized.

With reference to FIG. 5, the container bottom wall 34 encloses the bottom of the container. The container bottom wall connects with a container peripheral wall 86 which extends peripherally around the container bottom wall. Projections 87 define a horizontal vent path portion over the container upper lip and projections 88 define a vertical vent path portion along the side of the container so that the sterilant and rinse liquids can displace the ambient air. Moreover, the container and cover peripheral walls define the horizontal and vertical portions of the vent path 48 sufficiently tortuously that air born microbes are not carried into the container interior through the vent path.

The baffle plate 44 has a plurality of apertures 90 distributed therearound. The apertures are disposed offset from the inlet aperture 28. In this manner, the tortuous path 40 which is defined between the inlet aperture and the baffle plate nozzle apertures is sufficiently tortuous that air borne microbes are inhibited from entering the container. The baffle plate includes a plurality of projections 92 which project downward toward the container bottom wall to maintain the baffle plate and the container in the spaced relationship. The baffle plate also defines a canted surface section 94 adjacent the drain outlet. The canted surface portion extends over the drain outlet and provides fluid flow paths towards either edge thereof. Preferably, the canted portion is symmetrically disposed over the outlet aperture 46. Liquid then flows to the edges of the canted portion onto the lower surface 34 and down to the drain aperture 46. In this manner, a tortuous path is again defined between the drain aperture and the interior of the container. Projections 96 provide a barrier between the inlet and outlet passages so that the liquid pumped into the inlet flows through the baffle plate nozzle apertures primarily rather than directly to the outlet. A small vent passage 98 is defined through the barrier to assure that no ambient air is trapped adjacent the vent outlet and to thoroughly drain the baffle interspace during draining cycles. When the pump 54 is activated, some liquid will, of course, flow through this barrier vent but the majority will be discharged through the baffle plate apertures 90.

A pair of handles 100 are interconnected with the container lower portion to facilitate lifting of the container without accidental removal of the container cover.

The invention has been described with reference to the preferred embodiment. Obviously, modifications and alterations will occur to others upon reading and understanding the preceding detailed description. For example, the bottom wall and the baffle plate may be designed with appropriate ridges, partitions, depressions, and the like such that the container is dedicated to accommodating a preselected type of medical apparatus, items, or other equipment. Larger and smaller containers may also be provided. A plurality of smaller containers might even be provided within the basin and have their contents sterilized concurrently. It is intended that the invention be construed as including all such alterations and modifications insofar as they come within the scope of the appended claims or the equivalents thereof.

Having thus described the preferred embodiment, the invention is now claimed to be:

1. A liquid microbial decontamination system comprising:
   a basin which defines (i) a basin vent aperture adjacent an upper most portion thereof, (ii) a basin drain aperture adjacent a lower most portion thereof, and (iii) a basin liquid inlet;
   a lid for selectivley sealing the basin when in a closed position and providing ready access to the basin in an open position;
   a container for receiving articles to be microbially decontaminated removably disposed in the basin, the container defining a container liquid inlet, a container liquid outlet, and a nozzle plate which defines a tortuous inlet path between the container liquid inlet and a plurality of nozzles defined in and distributed around the nozzle plate, the tortuous inlet path being sufficiently tortuous that a migration of contaminating microbes in ambient air after removal from the basin is inhibited;
   a liquid antimicrobial solution supply means for supplying a liquid antimicrobial solution;
   a rinse supply means for supplying a rinse liquid;
   a drain operatively connected with the basin drain aperture for draining the antimicrobial solutions and rinse liquids from the basin;
   a means for selectivley opening and closing the drain to drain liquid form the basin and to retain liquid in the basin; and,
   a pumping means for selectivley pumping volumes of liquid antimicrobial solution from the liquid antimicrobial solution supply means and rinse liquid from the rinse supply means to the basin liquid inlet for selectivley filling the container and displacing ambient air therefrom.

2. A liquid microbial decontamination system comprising:
   a basin which defines (1) a basin vent aperture adjacent an upper most portion thereof, (ii) a basin adjacent a lower most portion thereof, and (iii) a basin liquid inlet;
   a lid for selectivley sealing the basin when in a closed position and providing ready access to the basin in an open position;
   a container for receiving articles to be sterilized removably disposed in the basin, the container including:
      a lower container portion having a bottom surface and a lower peripheral wall, the lower container portion defining a container drain aperture adjacent the basin lower most portion adjacent a junction between the bottom surface and the peripheral wall adjacent a first end of the lower container portion and defining a container liquid receiving aperture in the bottom surface in fluid communication with the basin liquid inlet,
      a container cover having a top surface and a downward depending cover peripheral wall which engages the lower container portion to close the container, the lower container portion and the cover being configured to define a tortuous vent path therebetween to the basin such that received liquids displace substantially all air from the container through the vent path;
   a liquid antimicrobial solution supply means for supplying a liquid antimicrobial solution;
   a rinse supply means for supplying a rinse liquid;
   a means for selectivley opening and closing the basin drain to drain liquid from the basin and to retain liquid in the basin; and,
   a pumping means for selectivley pumping volumes of liquid antimicrobial solution from the liquid antimicrobial solution supply means and rinse liquid from the rinse supply means to the basin liquid inlet for selectivley filling the container and displacing ambient air therefrom, the rinse supply means is connected with a tubing assembly which connects the pump with the basin liquid inlet in such a manner that all tubing and surfaces between the rinse supply means and the basin liquid inlet are microbially decontaminated by liquid antimicrobial solution circulated by the pump, whereby the rinse liquid passes only over microbially decontaminated surfaces as it passes from the rinse supply means to the basin liquid inlet.

3. A liquid microbial decontamination system comprising:
   a sloping basin which defines (i) a basin vent aperture adjacent an upper most portion thereof, (ii) a basin drain adjacent a lower most portion thereof, and (iii) a basin liquid inlet;
   a lid for selectivley sealing the basin when in a closed position and providing ready access to the basin in an open position;
   a container for receiving articles to be microbially decontaminated removably disposed in the basin, the container including:
      a lower container portion having a bottom surface and a peripheral wall, the lower container portion defining a container drain aperture adjacent he basin lower most portion adjacent a junction between the bottom surface and the peripheral wall adjacent a first end of the lower container portion and defining a container liquid receiving aperture in the bottom surface in fluid communication with the basin liquid inlet;

a nozzle plate which defines a tortuous inlet path between the container liquid receiving aperture and a plurality of nozzles defined in and distributed around the nozzle plate, the tortuous inlet path being sufficiently tortuous that a migration of contaminating microbes in ambient air after removal from the basin is inhibited;

a container cover having a top surface and a downward depending peripheral wall which engages the lower container portion to close the container, at least one of the lower container portion and cover being configured to define a tortuous container vent path from at least an upper most portion of the container to the basin such that received liquids displace substantially all air from the container through the container vent path;

a liquid antimicrobial solution supply means for supplying a liquid antimicrobial solution;

a rinse supply means for supplying a rinse liquid;

a means for selectivley opening and closing the basin drain to drain liquid from the basin and to retain liquid in the basin; and, a pumping means for selectively pumping volumes of liquid antimicrobial solution from the liquid antimicrobial solution supply means and rinse liquid from the rinse supply means to the basin liquid inlet for selectively filling the container and displacing ambient air therefrom.

4. The system set forth in claim 3 wherein the nozzle plate includes a generally flat surface in which an array of the nozzles is defined, all nozzles being offset from and out of alignment with the container liquid receiving aperture and container drain aperture such that there is no straight flow path through the container liquid receiving aperture, the container drain aperture, and one of the nozzles.

5. The system as set forth in claim 4 wherein the nozzle plate further includes a canted portion extending over the container drain aperture, the nozzle plate being mounted in a spaced relationship from the lower container portion bottom surface such that liquid flowing into the container liquid receiving aperture can flow through a narrow passage between the lower container portion bottom surface and the nozzle plate to the nozzles, the nozzle plate canted portion defining at least one passage to provide access to the container drain aperture for draining fluids from above the nozzle plate.

6. The system as set forth in claim 5 further including a partition means extending between the nozzle plate and the lower container portion bottom surface between the container liquid receiving aperture and the container drain aperture to inhibit fluid from flowing directly from the container liquid receiving aperture to the container drain aperture.

7. The system as set forth in claim 6 wherein the partition includes an additional vent aperture therethrough to prevent air from becoming trapped adjacent the container drain aperture between the lower container portion bottom surface and the nozzle plate.

8. The system as set forth in claim 3 wherein the cover downward depending flanges form a peripheral wall which circumscribes the lower container portion peripheral wall spaced therefrom at least in part to defined the container vent path.

9. The system as set forth in claim 8 further including spacers mounted to at least one of the lower container portion and cover peripheral walls to hold the lower container portion and cover peripheral walls in a spaced relationship defining the container vent path to allow air to escape and enable full filling of the container.

10. The system as set forth in claim 3 wherein the cover is transparent such that items held therein can be viewed from its exterior without removing the cover and disrupting a decontaminated state of the contained items.

11. The system as set forth in claim 3 further including instrument holders disposed on the nozzle plate for supporting and retaining items to be mcirobially decontaminated.

12. The system as set forth in claim 3 further including a handle means for assisting an operator to engage and lift the lower container portion without disturbing the cover.

13. In a sterilizing system that includes a sloping basin which defines a basin vent aperture adjacent a basin upper most portion, a basin drain aperture adjacent a basin lower most portion, and a basin liquid inlet; a lid for selectivley sealing the basin in a closed position and for providing access to the basin in an open position; a liquid sterilant supply means for supplying a liquid sterilant; a rinse supply means for supplying a rinse liquid; a drain operatively connected with the basin drain aperture for draining sterilant and rinse liquids from the basin; a tubing system interconnecting the liquid sterilant supply means, the rinse supply means, and the basin liquid inlet; a valve for selectivley opening and closing the drain to drain liquid from the basin and retain liquid in the basin; and, a pumping means operatively connected with the tubing system for selectivley pumping volumes of liquid sterilant, the container comprising:

a lower container portion removably disposed in the basin, the lower container portion having a bottom surface and a peripheral wall, the lower container portion defining a container drain aperture adjacent the basin lower most portion adjacent a junction between the bottom surface and the peripheral wall adjacent a first end of the lower container portion and defining a container liquid receiving aperture in the bottom surface in fluid communication with the basin liquid inlet;

a nozzle plate which defines a tortuous inlet path between the container liquid receiving aperture and a plurality of nozzles defined n and distributed around the nozzle plate, the nozzle plate tortuous inlet path being sufficiently tortuous that a migration of contaminating microbes in ambient air after removal from the basin is inhibited;

a container cover having a top surface and a downward depending peripheral wall which engages the lower container portion to close the container, at least one of the lower container portion and cover being configured to define a tortuous vent path from at least an upper most portion of the container to the basin such that received liquids displace substantially all air from the container through the tortuous vent path.

14. A container for holding items to be disinfected or sterilized, the container comprising:

a lower container portion having a bottom surface and a lower container portion peripheral wall, the lower container portion defining a drain aperture adjacent a junction between the bottom surface and the peripheral wall adjacent a first end of the lower container portion and defining a liquid receiving aperture in the bottom surface;

a nozzle plate which defines a tortuous inlet path between the liquid receiving aperture and a plurality of nozzles defined in and distributed around the nozzle plate, the tortuous inlet path being sufficiently tortuous that a migration of contaminating microbes in ambient air is inhibited;

a container cover having a top surface and a downward depending cover peripheral wall which engages the lower container portion to close the container, at least one of the lower container portion and cover being configured to defined a tortuous vent path from a second end opposite the first end such that received liquids displace substantially all air from the container through the tortuous vent path.

15. The container set forth in claim 14 wherein the nozzle plate includes a generally flat surface in which an array of nozzle apertures is defined, all nozzle apertures being offset from and out of alignment with the liquid receiving and drain apertures such that there is no straight flow path through the liquid receiving aperture, the drain aperture, and one of the nozzle apertures.

16. The container as set forth in claim 15 wherein the nozzle plate further includes a canted portion extending over the drain aperture, the nozzle plate being mounted in a spaced relationship from the bottom surface such that liquid flowing into the liquid receiving aperture can flow through a narrow passage between the bottom surface and the nozzle plate to the nozzle apertures, the nozzle plate canted portion defining at least one passage into the narrow space between the nozzle plate and the bottom surface to provide access to the drain aperture.

17. The container as set froth in claim 16 further including a partition means extending between the nozzle plate and the bottom surface between the liquid receiving aperture and the drain aperture to inhibit fluid from flowing directly from the liquid receiving aperture to the drain aperture.

18. The container as set forth in claim 17 wherein the partition includes a partition vent aperture therethrough to prevent air from becoming trapped adjacent the drain aperture between the bottom surface and the nozzle plate.

19. The container as set forth in claim 14 wherein the cover downward depending peripheral wall circumscribes the lower container portion peripheral wall in a spaced relationship at least in part to define the tortuous vent path.

20. The container as set forth in claim 19 further including spacers mounted to one of the lower container portion and cover peripheral walls to hold the lower container portion and cover peripheral walls in the spaced relationship.

21. The container as set forth in claim 14 wherein the cover is transparent such that items held therein can be viewed from its exterior without removing the cover and disrupting a disinfected or sterile state of the contained items.

22. The container as set forth in claim 14 further including instrument holders disposed on the nozzle plate for supporting and retaining items to be disinfected or sterilized.

23. The container as set forth in claim 14 further including a handle means for assisting an operator to engage and lift the lower container portion without disrupting the cover.

* * * * *